United States Patent [19]

Mayama et al.

[11] 3,962,419
[45] June 8, 1976

[54] STABILIZED ANTIBIOTIC SF-837 PREPARATION

[75] Inventors: Takeshi Mayama, Chigasaki; Toshiyuki Kobayashi, Kawasaki; Akira Okada, Zushi, all of Japan

[73] Assignee: Meiji Seika Kaisha, Ltd., Japan

[22] Filed: Aug. 9, 1974

[21] Appl. No.: 496,299

Related U.S. Application Data

[63] Continuation of Ser. No. 241,418, April 5, 1972, abandoned.

[30] Foreign Application Priority Data

Apr. 15, 1971 Japan.................... 46-23452

[52] U.S. Cl.................... 424/78; 424/35; 424/115

[51] Int. Cl.² ................ A61K 9/36; A61K 31/765; A61K 35/00

[58] Field of Search ............ 424/32, 78, 81, 35, 424/115

[56] References Cited

UNITED STATES PATENTS

| | | | |
|---|---|---|---|
| 3,576,760 | 4/1971 | Gould et al. | 424/32 |
| 3,608,063 | 9/1971 | Banker | 424/32 |
| 3,629,392 | 12/1971 | Banker | 424/32 |
| 3,691,090 | 9/1972 | Kitajima | 424/32 |
| 3,829,564 | 8/1974 | Merry et al. | 424/32 |

*Primary Examiner*—Sam Rosen
*Attorney, Agent, or Firm*—McGlew and Tuttle

[57] ABSTRACT

This invention relates to an antibiotic preparation comprising a macrolide antibiotic, which is highly stabilized against an acidic solution or acidic substance because of the presence of a polymer component incorporated with the macrolide antibiotic by specific solvent treatment, and to a process for the production of such antibiotic preparation. The antibiotic preparation of this invention overcomes the defect of macrolide antibiotics that they are easily decomposed upon contact with an acidic solution or acidic substance.

4 Claims, No Drawings

STABILIZED ANTIBIOTIC SF-837 PREPARATION

This is a continuation of application Ser. No. 241,418, filed Apr. 5, 1972, now abandoned.

This invention relates to an effective and valuable medicinal preparation applicable to remedy for diseases caused by bacteria sensitive to macrolide antibiotics. More particularly, the invention relates to a process for stabilization of medicinal preparations containing macrolide antibiotics.

Macrolide antibiotics, such as kitasamycin, erythromycin, spiramycin, josamycin, and antibiotic SF-837 have a medium antimicrobial spectrum, and are useful antibiotics which can be applied by oral, rectal or vaginal administration with low toxicity. However, these antibiotics are unstable in acidic solutions (see Ichimaro Ichino et al, "Handbook of Antibiotics" published by Sangyo Tosho Kabushiki Kaisha, pages 59–60). Accordingly, in case an organic acid such as citric acid is added to a medicinal preparation containing any of these antibiotics, for instance, syrups, for the purpose of improving taste, decomposition of the antibiotic is accelerated. Also when other acidic substances such as ascorbic acid and acetylsalicylic acid are incorporated, the antibiotic are likely to be decomposed.

Further, these antibiotics, even in powdery state, will likely absorb moisture during the lapse of time, thus readily undergo decomposition upon contact with an acidic substance.

Having made an intensive research on medicinal preparation of macrolide antibiotics, the inventors succeeded in providing a medicinal preparation of a macrolide antibiotic which is stable against acidic media.

Accordingly, the primary object of this invention is to provide a stabilized preparation of a macrolide antibiotic which is stable against an acidic solutions and an acidic substance.

Another object of this invention is to provide a process for manufacturing a macrolide antibiotic preparation which is stable against acidic solutions and an acidic substances.

Other objects and advantages of this invention will be apparent from the description given hereinbelow.

In accordance with this invention, there is provided a stabilized antibiotic preparation which comprises at least 50% by weight of a macrolide antibiotic as an effective substance and a polymer insoluble in acidic solutions, by applying a minimum amount of solvent capable of dissolving the said polymer, and dry off said solvent from the resulting solution or suspension containing said antibiotic and polymer.

This invention will now be described in more detail. The medicinal preparation of this invention comprises at least 50% by weight of an antibiotic substance such as kitasamycin, erythromycin, spiramycin, josamycin or antibiotic SF-837 as the effective substance and a polymer insoluble in acidic solutions. As such polymer insoluble in acidic solutions there may be exemplified cellulose acetate phthalate, hydroxypropyl methylcellulose phthalate and a methyl acrylate-methacrylic acid copolymer. Preferable contents of the polymer in the dry product composed of the macrolide antibiotic and the polymer is within the range of from 10 to 20% by weight. In addition to the above effective substance, the medicinal preparation of this invention may further comprise adjuvants, corrigents, vehicles, and other additives customarily used in the pharmaceutical industry. The medicinal preparation can be applied in the form of syrups, powders, granules, capsules, tablets, suppositories and the like.

The effective medicinal preparation of this invention can be prepared according to the following procedure.

A macrolide antibiotic and a polymer are incorporated into a solvent capable of dissolving the polymer. It is essential that the amount of the antibiotic used is such that its content in the resulting dry product is at least 50%, and that the amount of the solvent is at least such that capable of dissolving the polymer efficiently. As such solvents there may be exemplified are methanol, ethanol, isopropanol, acetone, ethyl acetate, methyl cellosolve, ethyl cellosolve, benzene, methylethylketone, carbon tetrachloride, chloroform, methylene chloride, trichloroethane and dichloroethane. They may be used alone, or as mixtures of two or more of them.

In this incorporation operation, the order of addition of the three components is not critical; they may also be introduced at the same time. The temperature of the resulting solution or suspension is not particularly critical, but it is prefereed that it is maintained at a temperature below the boiling point of the solvents.

The solvent is then evaporated and removed from the said solution or suspension containing the antibiotic and polymer to obtain a dry product.

Any of conventional drying methods may be adopted for evaporation and removal of the solvent; air-drying, drying under reduced pressure, spray drying or vacuum drum drying methods are among those preferred. The resulting dry product is pulverized, incorporated with adjuvants, corrigents, vehicles and other pharmaceutically acceptable additives, e.g., excipients, sweetening agents, lubricants, disintegrators and binders and formed into syrups, powders, granules, capsules, tablets, suppositories or the like, according to demand.

Thus, in accordance with this invention, there is also provided a process for manufacturing a stabilized antibiotic preparation, which comprises incorporating a macrolide antibiotic and a polymer insoluble in acidic solutions in a solvent capable of dissolving said polymer, the amount of said macrolide antibiotic is at least 50% by weight based on the total amount of the antibiotic and polymer, and the amount of the solvent is at least such that necessary for dissolving the polymer efficiently, evaporating and removing the solvent from the resulting solution or suspension, incorporating the remaining dry product pharmaceutically acceptable additives according to demand, and finally making the same into an pharmaceutically administrable form.

The stabilizing effect attained by this invention will now be explained by referring to one embodiment.

For instance, antibiotic SF-837, which is a macrolide antibiotic, and hydroxypropyl methylcellulose phthalate, which is a polymer insoluble in acid solutions, are mixed together to form a mixture in which the content of the former is 90% by weight and that of the latter is 10% by weight. Then chloroform is added to the mixture, and which is stirred to dissolve the antibiotic and polymer in the chloroform. Hot air is introduced to the solution to evaporate and remove the chloroform therefrom. The resulting dry product is pulverized according to demand, incorporated with other components, and made into a desired pharmaceutically applicable form. The so formed dry product retains 85% of the original antimicrobial activity even after being kept in water of a pH value of 2 at 37°C for 4 hours. In contrast, when antibiotic SF-837 alone is allowed to stand under the same conditions, the antimicrobial activity reduced to 68%. The antimicrobial activity is determined by means of bioassay with *Bacillus subtilis* as a test bacterium.

From the foregoing it can readily be understood that the method of stabilizing macrolide antibiotics against acidic media according to this invention is prominently excellent and that the stabilized macrolide antibiotic preparation is very useful owing to its high stability against acidic media.

This invention will now be described by the following examples, but the scope of this invention is not at all limited by them.

EXAMPLE 1

To a mixture of 900g of antibiotic SF-837 and 100g of cellulose acetate phthalate, 1,200 ml of chloroform is added. When the mixture is completely dissolved, air-drying is conducted by introducing hot air (60°–80°C) into the solution. The resulting dry product is pulverized and suspended into a water or the like to form a syrup. When the so formed stabilized antibiotic SF-837 preparation is kept in water of a pH value of 2.0 at 37°C for 4 hours, it retains 88% of its original antimicrobial activity. In contrast, when antibiotic SF-837 is allowed to stand under the same conditions, its antimicrobial activity is reduced to 68%. The antimicrobial activity is determined according to the bioassay with *Bacillus subtilis* at a test bacterium.

EXAMPLE 2

800g of antibiotic SF-837 is well mixed with 200g of hydroxypropyl methylcellulose phthalate, and 2,000 ml of a mixed liquor of equal amounts of acetone and methanol is added. When the mixture is dissolved, the resulting solution is subjected to the spray drying. The dry product is incorporated, according to need, with other material (such as an excipient, e.g., starch or lactose, a sweetening agent, a lubricant, a disintegrator, a binder or the like), and filled in capsules and applied in the form of capsules.

EXAMPLE 3

950g of antibiotic SF-837 is incorporated with 500 ml of a solution of 50g of hydroxypropyl methylcellulose phthalate in methylene chloride, and well mixed to form a suspension. Methylene chloride is removed under reduced pressure to obtain a dry product. The dry product is pulverized, incorporated with corn starch and a small quantity of magesium stearate, and formed into tablets.

EXAMPLE 4

700g of antibiotic SF-837, 300g of a methyl acrylate-methacrylic acid copolymer and 2,000 ml of ethanol are blended together to form a solution. Afterwards, the ethanol is evaporated off from the solution by means of a vacuum drum drier. The resulting dry solid product is pulverized and formed into a powdery preparation.

When the powdery preparation is allowed to stand in water of a pH value of 2.0 at 37°C for 4 hours, it retains 91% of its original antimicrobial activity. The antimicrobial activity is determined according to the bioassay with *Bacillus subtilis* as a test bacterium.

EXAMPLE 5

90g of kitasamycin is well mixed with 10g of cellulose acetate phthalate. 150 ml of chloroform is added. When the mixture is completely dissolved, the chloroform is evaporated from the solution by introducing hot air (60°–80°C) to the solution. The dry product is pulverized and suspended in water or the like to form a syrup, whose antimicrobial activity retains 81% of the original even after being kept in water of a pH value of 2.0 at 37°C for 4 hours. In contrast, kitasamycin retains its antimicrobial activity only 53% under the same conditions. The antimicrobial activity is determined by the bioassay according to the method described in Japanese Standards of Antibiotic Preparations.

EXAMPLE 6

90g of josamycin is well mixed with 10g of hydroxypropyl methylcellulose phthalate. The mixture is dissolved in 200 ml of methylene chloride. By introducing hot air (60°–80°C), methylene chloride is evaporated and removed from the solution. The resulting dry product is pulverized and suspended in water or the like to form a syrup. The so formed josamycin preparation retains its antimicrobial activity 83% of the original even after being kept in water of a pH value of 2.0 at 37°C for 4 hours. In contrast, josamycin retains antimicrobial activity only 57% under the same conditions. The antimicrobial activity is determined by the bioassay according to the method described in Japanese Standards of Antibiotic Preparations.

EXAMPLE 7

80g of spiramycin is well mixed with 20g of hydroxypropyl methylcellulose phthalate, and the mixture is dissolved in 120 ml of methanol. The methanol is evaporated under reduced pressure and removed from the solution. The resulting dry product is pulverized and suspended in water or the like to form a syrup. This preparation of spiramycin retains 86% of the original antimicrobial activity even after it has been allowed to stand still in water of a pH of 2.0 at 37°C for 4 hours. In contrast, spiramycin retains only 51% of the antimicrobial activity under the same conditions. The antimicrobial activity is determined by the bioassay according to the method stipulated in Japanese Standards of Antibiotic Preparations.

EXAMPLE 8

70g of erythromycin is well mixed with 30g of cellulose acetate phthalate, and the mixture is dissolved in 200 ml of a mixed liquor of equal amounts of acetone and methanol. By introducing hot air (50°–80°C), the mixed liquor is evaporated and removed from the solution. The resulting dry product is pulverized and suspended in water or the like to form a syrup. This erythromycin preparation retains its antimicrobial activity 91% of the original even after it has been allowed to stand in water of a pH value of 2.0 at 37°C for 4 hours, whereas erythromycin alone retains only 50% under the same conditions. The antimicrobial activity is determined by the bioassay according to the method stipulated in Japanese Standards of Antibiotic Preparations.

We claim:
1. A stabilized antibiotic preparation containing (1) at least 50% by weight of a macrolide antibiotic consisting essentially of antibiotic SF-837 incorporated into

(2) a stabilizing amount of a polymer insoluble in acidic solutions consisting essentially of hydroxypropyl methylcellulose phthalate.

2. A stabilized antibiotic preparation according to claim 1, wherein the content of the polymer insoluble in acidic solutions is within the range of from about 10 to about 20% by weight.

3. A stabilized antibiotic preparation according to claim 1, which further comprises pharmaceutically acceptable substances selected from adjuvants, corrigents, vehicles, excipients, sweetening agents, disintegrators, lubricants and binders.

4. A stabilized antibiotic preparation according to claim 1, which is in the form of syrup, powder, granule, capsule, tablet or suppository.

* * * * *